(12) United States Patent
Kim et al.

(10) Patent No.: US 10,274,407 B2
(45) Date of Patent: Apr. 30, 2019

(54) METHOD OF EVALUATING STRETCH-FLANGEABILITY WITH SMALL-SCALE SPECIMEN WITHOUT SPECIMEN SIZE EFFECTS

(71) Applicant: POSTECH ACADEMY-INDUSTRY FOUNDATION, Pohang-si (KR)

(72) Inventors: Hyoung Seop Kim, Pohang-si (KR); Jae Ik Yoon, Pohang-si (KR); Hak Hyeon Lee, Ulsan (KR); Jaimyun Jung, Seoul (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 15/977,030

(22) Filed: May 11, 2018

(65) Prior Publication Data
US 2018/0328826 A1 Nov. 15, 2018

(30) Foreign Application Priority Data
May 11, 2017 (KR) .................. 10-2017-0058548

(51) Int. Cl.
*G01N 3/00* (2006.01)
*G01N 3/28* (2006.01)
*G06F 17/50* (2006.01)

(52) U.S. Cl.
CPC ............ *G01N 3/28* (2013.01); *G06F 17/50* (2013.01); *G01N 2203/0067* (2013.01);
(Continued)

(58) Field of Classification Search
CPC ............ G01N 3/28; G01N 2203/0067; G01N 2203/0212; G01N 2203/0218;
(Continued)

(56) References Cited

U.S. PATENT DOCUMENTS 4,501,626 A * 2/1985 Sudo .................. B01D 39/2086
148/320
6,364,968 B1 * 4/2002 Yasuhara .................. C21D 1/20
148/320
(Continued)

*Primary Examiner* — Max H Noori
(74) *Attorney, Agent, or Firm* — Lex IP Meister, PLLC

(57) ABSTRACT

A method according to the present invention, it is possible to accurately measure the stretch-flangeability of sheet metal materials without size effects even when a small amount of specimen is used, compared with the stretch-flangeability established as an international standard, and to measure the stretch-flangeability in the local region. The method according to the present invention includes (a) performing a computer simulation of a small-scale specimen having a predetermined size by using finite element analysis to determine a size of the small-scale specimen; (b) using a standard-scale specimen having the same material as the small-scale specimen specified in the step (a) to perform a punching process specified in the standard testing method; (c) observing a distribution pattern of shearing defects in a hole-edge region of the specimen having performed the punching process, and evaluating a hole expansion ratio; (d) comparing the hole expansion ratio and the distribution pattern of shearing defects between the small-scale specimen and the standard-scale specimen to verify measurement reliability for the stretch-flangeability of the small-scale specimen; and (e) using the size of the small-scale specimen having verified the measurement reliability to evaluate stretch-flangeability.

9 Claims, 8 Drawing Sheets

(52) U.S. Cl.
CPC ............... *G01N 2203/027* (2013.01); *G01N 2203/0212* (2013.01); *G01N 2203/0218* (2013.01); *G01N 2203/0282* (2013.01); *G01N 2203/0286* (2013.01)

(58) Field of Classification Search
CPC ..... G01N 2203/027; G01N 2203/0282; G01N 2203/0286; G06F 17/50
USPC .......................................................... 73/794
See application file for complete search history.

(56) References Cited

U.S. PATENT DOCUMENTS

| | | | | |
|---|---|---|---|---|
| 7,468,109 | B2 * | 12/2008 | Kashima | B32B 15/012 148/320 |
| 8,511,178 | B2 * | 8/2013 | Golovashchenko | G01N 3/20 73/849 |
| 2004/0118489 | A1 * | 6/2004 | Sun | C21D 8/021 148/602 |
| 2009/0050244 | A1 * | 2/2009 | Nakagawa | C21D 8/0205 148/602 |
| 2009/0136378 | A1 * | 5/2009 | Satou | C21D 9/46 420/91 |

* cited by examiner

[FIG.1]
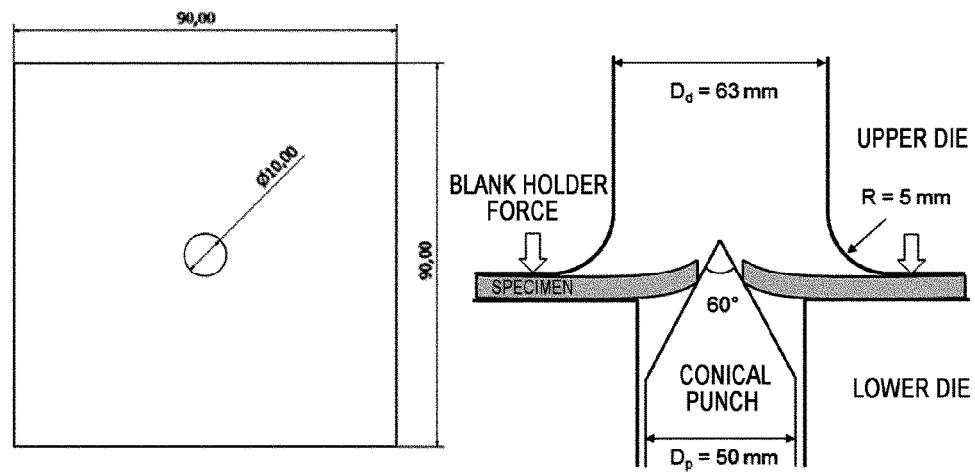
[FIG.2]
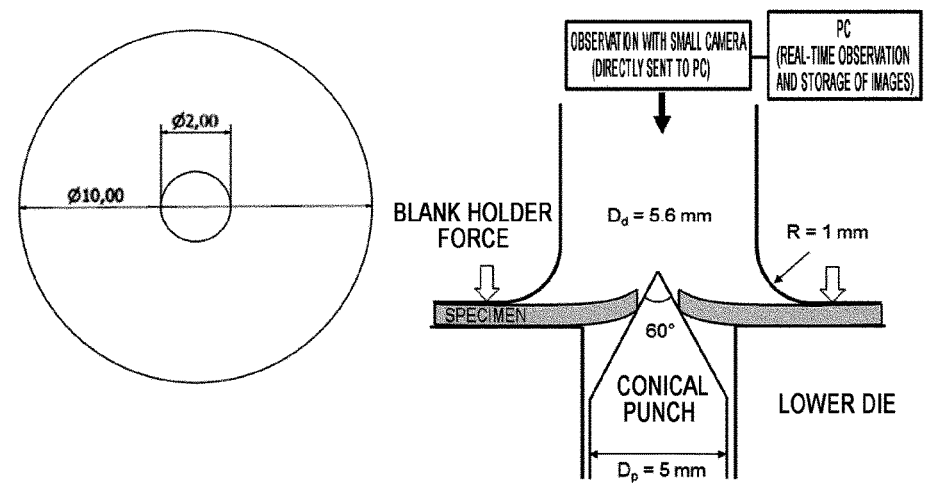

[FIG.3(a)]
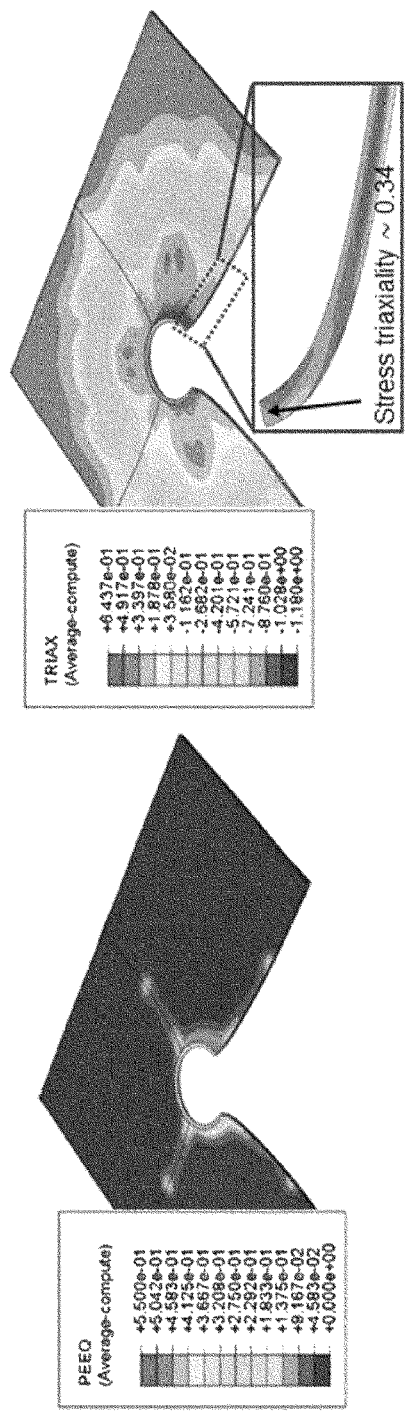

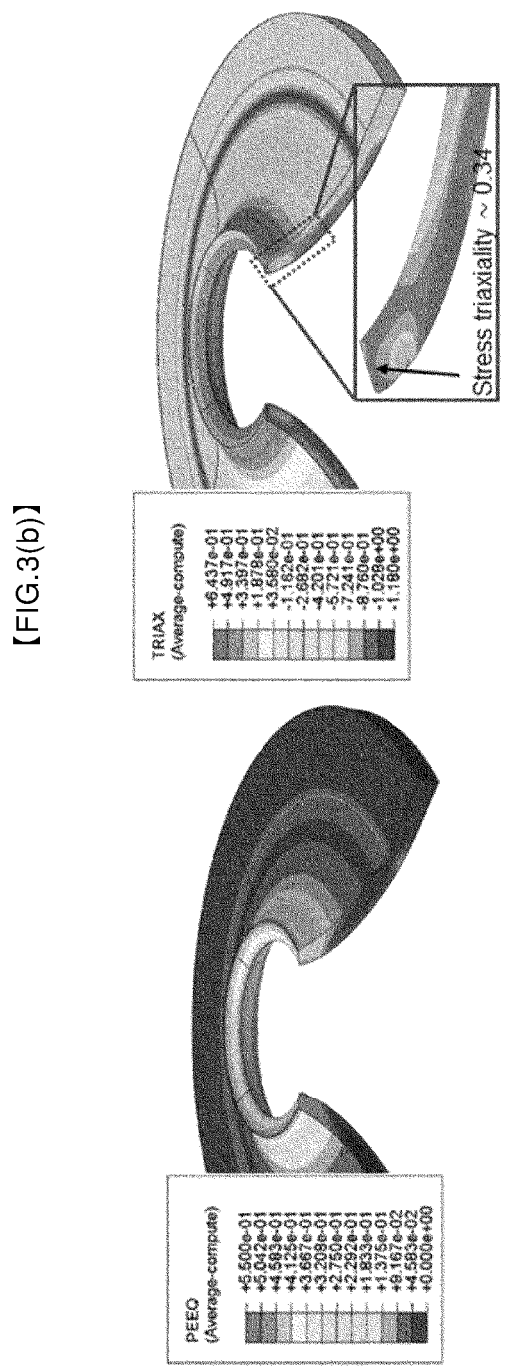
[FIG.3(b)]

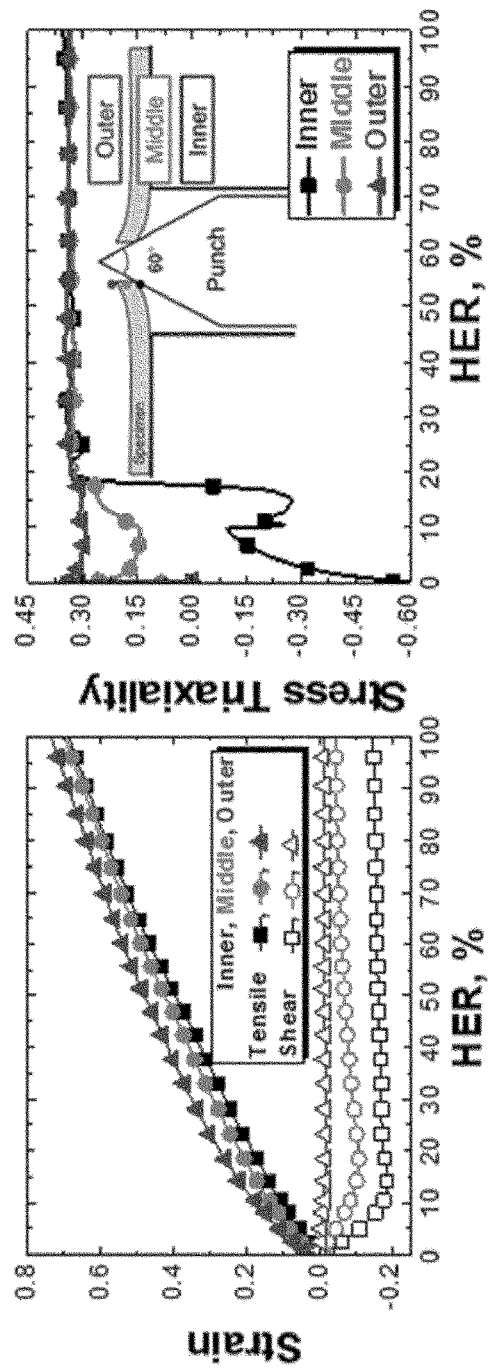
[FIG.4(a)]

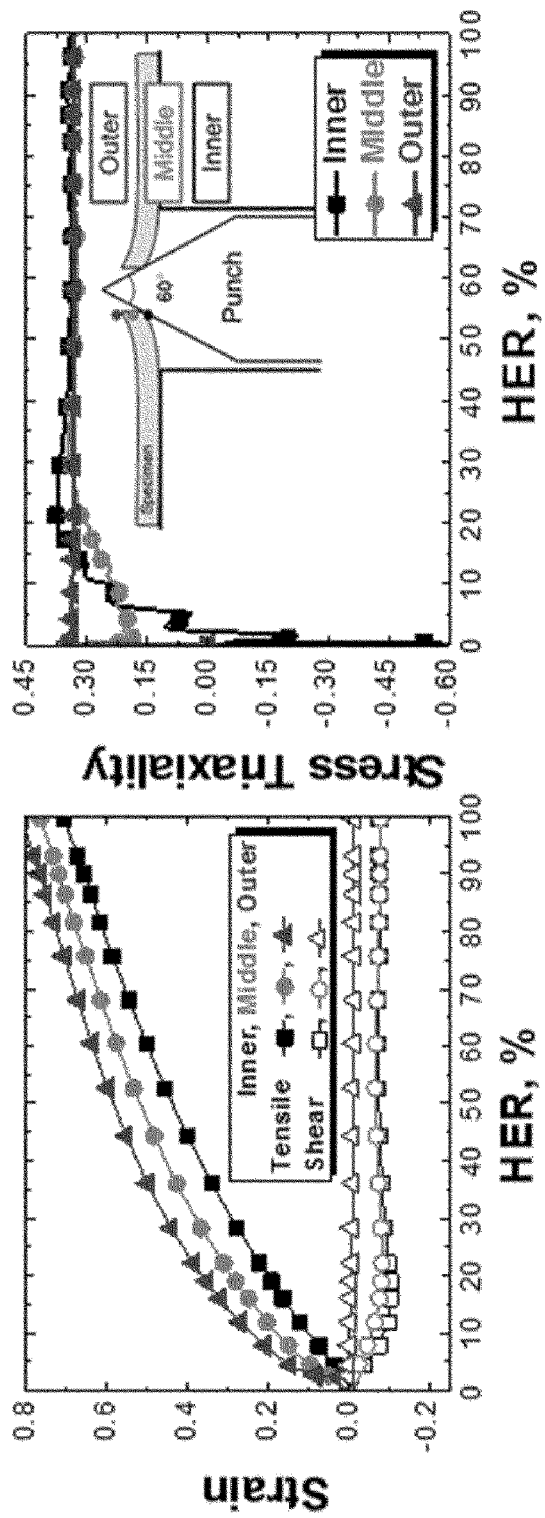
[FIG.4(b)]

[FIG.5(a)]
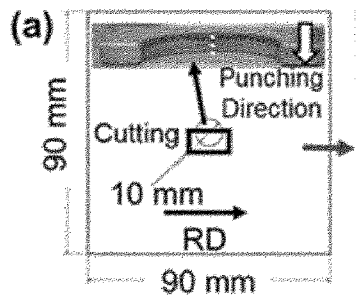
[FIG.5(b)]
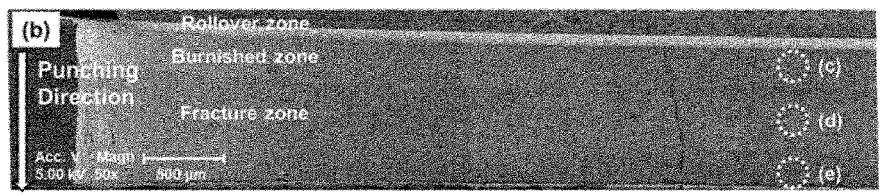
[FIG.5(c)]
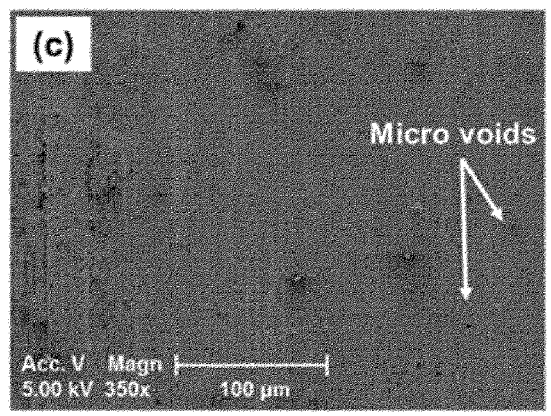
[FIG.5(d)]
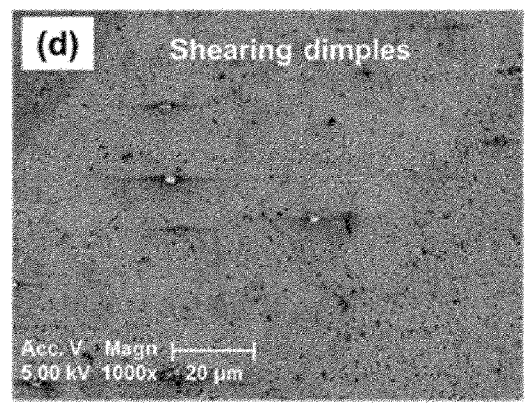

【FIG.5(e)】
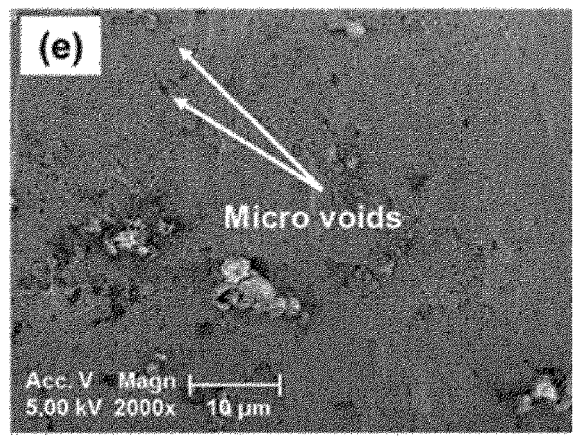
【FIG.6(a)】
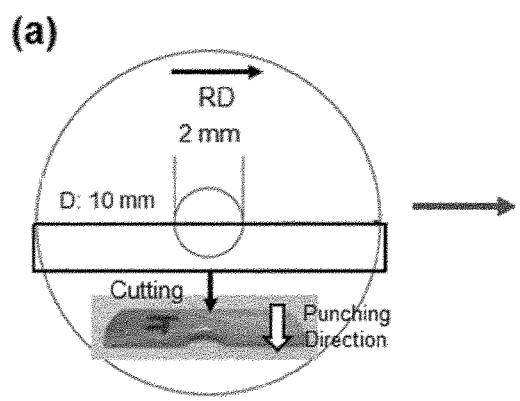
【FIG.6(b)】
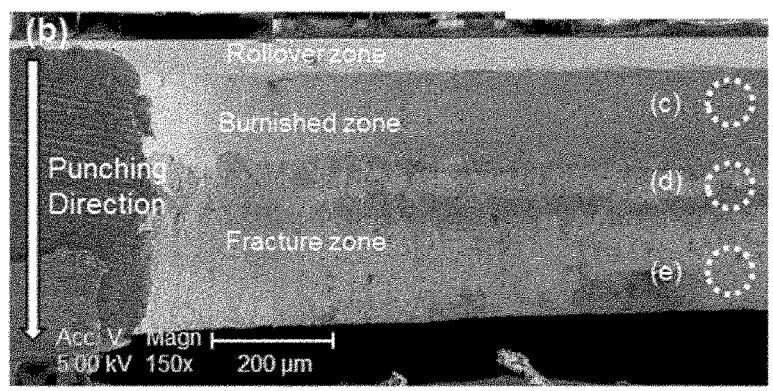

[FIG.6(c)]
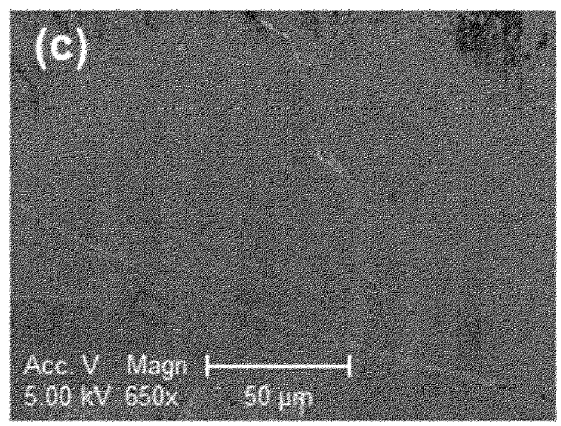
[FIG.6(d)]
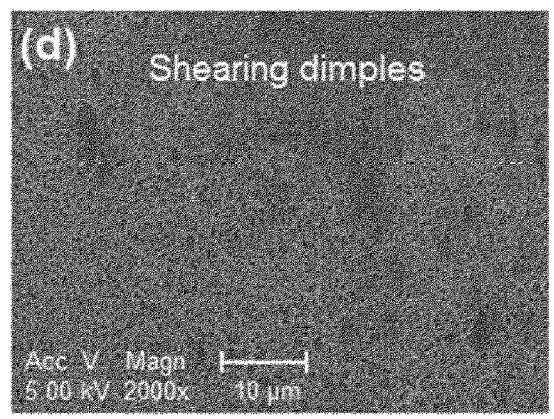
[FIG.6(e)]
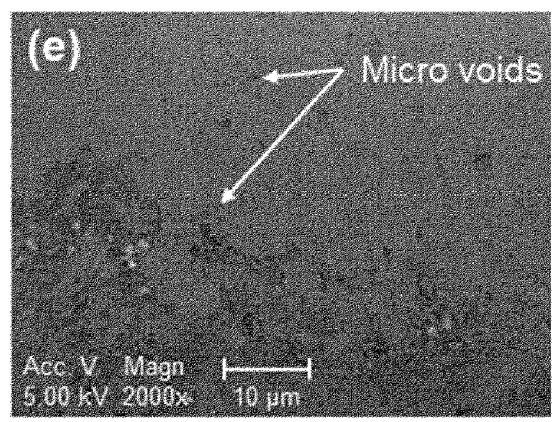

METHOD OF EVALUATING STRETCH-FLANGEABILITY WITH SMALL-SCALE SPECIMEN WITHOUT SPECIMEN SIZE EFFECTS

BACKGROUND OF THE INVENTION

1. Field of the Invention

The present invention relates to a method of evaluating an accurate stretch-flangeability of a sheet metal material with a small-scale specimen. Specifically, the present invention relates to a method of evaluating stretch-flangeability of obtaining the same value as in the measurement of using a standard-scale specimen without the specimen size effects which are an important factor in the formability test and differ in formability evaluation result depending on a specimen size, even when the specimen size is reduced as compared with the standard-scale specimen in the hole expansion test which is the ISO 16630 international standard stretch-flangeability evaluation method.

2. Description of the Related Art

To prepare the trend towards more demanding environmental and safety regulations worldwide, the automobile industry has continued to reduce the weight of body-in-white components and to increase their stability by using advanced high-strength steel sheets for automotive components.

The areas where the weight is reduced drastically by applying advanced high-strength steels are chassis components such as wheels, discs, lower arms and the like of automobiles. In order to apply advanced high-strength steel sheets to such chassis components, the stretch-flangeability, which is a formability index representing the ability to resist edge fracture in the complex forming process, is a very important factor.

Stretch-flangeability, which is an important formability index in that sheet metal materials are applied to the automobile components, is measured by the hole expansion ratio (HER) according to the ISO 16630 international standard evaluation method.

However, in the case of the standard evaluation method, an excessively large-sized specimen is required in comparison with evaluation methods for other mechanical properties, so that there is a disadvantage in that the stretch-flangeability of steel in the development stage in which a sheet steel is not mass produced and the local stretch-flangeability of the sheet material may not be measured.

In addition, due to the standard evaluation method of requiring a large-sized specimen for the stretch-flangeability evaluation, it may take a long time for evaluation and feedback of the stretch-flangeability in development of advanced high-strength steel sheets to be applied to automobile components.

PRIOR ART DOCUMENT

Non-Patent Document

ISO 16630:2009, Metallic Materials—Sheet and strip—Hole expanding test, International Organization for Standardization, http://www.iso.org (2009).

Y. Bao, T. Wierzbicki, On fracture locus in the equivalent strain and stress triaxiality space, Int. J. Mech. Sci. 46 81-98 (2004).

Y. Bai, T. Wierzbicki, Application of extended MohrCoulomb criterion to ductile fracture, Int. J. Fracture 161 1-20 (2010).

N. Bonora, D. Gentile, A. Pirondi, G. Newaz, Ductile damage evolution under triaxial state of stress: Theory and experiments, Int. J. Plasticity 21 981-1007 (2005).

SUMMARY OF THE INVENTION

The present invention addresses the above-identified, and other problems associated with conventional methods and apparatuses.

According to an embodiment of the invention, there is provided a method of evaluating reliably and economically stretch-flangeability of a sheet metal material without specimen size effects even while using a substantially small-scale specimen, in comparison with a standard-scale specimen.

According to an embodiment of the invention, there is provided a method of evaluating stretch-flangeability with a small-scale specimen without specimen size effects, including: (a) performing a computer simulation of a small-scale specimen having a predetermined size by using finite element analysis to determine a size of the small-scale specimen; (b) using a standard-scale specimen having the same material as the small-scale specimen determined in the step (a) to perform a punching process specified in a standard testing method; (c) observing a distribution pattern of shearing defects in a hole-edge region of the specimen having performed the punching process, and to evaluate a hole expansion ratio; (d) comparing the hole expansion ratio and the distribution pattern of shearing defects between the small-scale specimen and the standard-scale specimen to verify measurement reliability for the stretch-flangeability of the small-scale specimen; and (e) using a size of the small-scale specimen having verified the measurement reliability to evaluate stretch-flangeability.

In a preferred embodiment of the invention, the step (a) may include analyzing a stress triaxiality of deformation behavior in the hole expansion test of the standard-scale specimen through a computer simulation using finite element analysis to be used as a standard deformation behavior; and analyzing the stress triaxiality of the deformation behavior at the hole expansion test of the small-scale specimen to verify a morphology and a size validity of the small-scale specimen through comparison with the standard-scale specimen.

In a preferred embodiment of the invention, in the step (a), the radius of an initial hole of the small-scale specimen may be within ¼ of the distance from a center of the initial hole-edge to an edge of the specimen, wherein the punch having a conical angle of 60° used in hole expansion has a diameter in the range of 1.5 times to 10 times the initial hole diameter.

In a preferred embodiment of the invention, the deformation behavior of the small-scale specimen simulated by the computer simulation is compared with and the deformation behavior of the standard-scale specimen, and when not similar, the size may be adjusted and repeated until being similar, whereby the size of the small-scale specimen is determined.

In a preferred embodiment of the invention, in the step (a), the minimum value of the thickness of the small-scale specimen may be 10 times or more the grain size of the material to be evaluated.

This is to prevent grain size effects which cause a difference in mechanical properties when the number of grains is too small in the thickness direction. Also, this is because the thickness of 10 times or less the grain size of the evaluation material is more preferably excluded from the evaluation range even when the deformation behavior through the analysis of the stress triaxiality is similar.

In a preferred embodiment of the invention, when the deformation behavior of the small-scale specimen is analyzed by the hole expansion test in the computer simulation, the small-scale specimen may be evaluated to have a similar deformation behavior to the deformation behavior in the hole expansion test of the standard-scale specimen when stress triaxialities in all of the inner, middle and outer areas are within 0.3 to 0.5 in the range of a hole expansion ratio of 20% or more.

In the standard hole expansion test, a uniaxial tensile deformation behavior is a dominant deformation behavior when a stress triaxiality is analyzed in the outer area where fracture is initiated. The uniaxial tensile deformation behavior has a dominant stress triaxiality in the range of 0.3 to 0.5. In the range where the hole expansion ratio at which most of sheet metal materials are fractured is 20% or more, the stress triaxiality in inner, middle and outer areas is within the range of 0.3 to 0.5. Accordingly, when the deformation behavior of the small-scale specimen is analyzed by the hole expansion test, and when the stress triaxiality in the outer area is within 0.3 to 0.5 and the stress triaxiality is within 0.3 to 0.5 in the inner, middle and outer areas in the range where the hole expansion ratio at which most of sheet metal materials are fractured is 20% or more, the small-scale specimen may be evaluated to have a similar deformation behavior to the deformation behavior in the hole expansion test of the standard-scale specimen. Further, on the basis of this, the thickness range of the small-scale specimen having a similar stress triaxiality to the case of hole expansion deformation may be found by comparing the stress triaxiality between the small-scale specimen and the standard-scale specimen.

In a preferred embodiment of the invention, the standard test method may be a method of measuring the standard stretch-flangeability of a sheet metal material, which is the ISO16630 hole expansion ratio test method.

In a preferred embodiment of the invention, in the step (c), the surface of shearing defects generated after the punching process may be fine and have steps, thus being difficult to be observed by an optical microscope, so that each part of the surface of the shearing defects in the hole-edge region may be observed through a scanning electron microscope (SEM).

In a preferred embodiment of the invention, in the step (d), the measurement reliability of the small-scale specimen is verified by comparing the distribution pattern of shearing defects and the evaluation results of hole expansion ratio of the small-scale specimen and the standard-scale specimen. In this case, the distribution pattern of shearing defects generated in an initial hole-edge region after the punching process is one of dominant factors of affecting the hole expansion ratio, so that when the hole expansion ratio is evaluated by using the small-scale specimen and the standard-scale specimen, the small-scale specimen may be evaluated to have reliability in the case of having the surface of shearing defects having a similar morphology and distribution to that shown in FIGS. 5 and 6 and Table 1.

In a preferred embodiment of the invention, when the measurement reliability of the step (d) is verified, the small-scale specimen may be evaluated to have reliability when the evaluation value for the hole expansion ratio of the small-scale specimen is 0.9 to 1.1 times the evaluation value of the standard-scale specimen.

BRIEF DESCRIPTION OF THE DRAWINGS

FIG. 1 is an illustrative view illustrating a specimen and an evaluation mold for evaluating the stretch-flangeability of a sheet metal material through a hole expansion test according to the ISO 16630 international standard (Dd: inner diameter of a mold in the hole expansion test, Dp: diameter of a punch in the hole expansion test);

FIG. 2 is an illustrative view illustrating a specimen and an evaluation mold for evaluating stretch-flangeability of a sheet metal material through a hole expansion test by utilizing a small-scale specimen without specimen size effects according to an embodiment of the invention;

FIGS. 3(a) and 3(b) are illustrative views of analyzing the deformation behavior of a standard-scale specimen (a), and a small-scale specimen (b) without specimen size effects according to the invention in the hole expansion test through a computer simulation using finite element analysis (PEEQ: equivalent plastic strain, TRIAX: stress triaxiality);

FIGS. 4(a) and 4(b) are graphs showing the deformation distribution of a hole-edge region depending on a hole expansion ratio of a standard-scale specimen (a), and a small-scale specimen (b) without specimen size effects according to the invention in the hole expansion test through a computer simulation using finite element analysis;

FIGS. 5(a), 5(b), 5(c), 5(d) and 5(e) are scanning electron microscope photographs of the initial hole-edge region manufactured by punching the center of a standard-scale specimen according to the ISO 16630 international standard; and FIGS. 6(a), 6(b), 6(c), 6(d) and 6(e) are scanning electron microscope photographs of the initial hole-edge region manufactured by punching the center of a small-scale specimen without specimen size effects according to the invention.

DETAILED DESCRIPTION OF THE EXEMPLARY EMBODIMENTS

Hereinafter, a method of stretch-flangeability with a small-scale specimen without specimen size effects according to a preferred embodiment of the invention will be described in detail with reference to the accompanying drawings, but the embodiment is not limited to the following examples. Therefore, it is obvious that the present invention may be modified in various forms within the scope without departing from the technical idea of the present invention by those skilled in the art.

FIG. 1 is an illustrative view illustrating a specimen and an evaluation mold for evaluating the stretch-flangeability of a sheet metal material through a hole expansion test according to the ISO 16630 international standard (in the drawing, Dd: inner diameter of a mold in the hole expansion test, Dp: diameter of a punch in the hole expansion test). As described in FIG. 1, a standard-scale specimen is large in size and requires large amounts of material in order to perform the test.

In the present invention, in order to obtain the results of the hole expansion test according to the standard-scale specimen even while not only using a small-scale specimen not to use large amounts of material like the standard-scale specimen of FIG. 1, but also having the degree of freedom in the morphology of the specimen, the reliability for the hole expansion test of the small-scale specimen was secured through a method of eliminating size effects caused by size reduction through the following procedures.

Computer Simulation Step

A computer simulation step is a step of preliminarily determining the size of a small-scale specimen by using finite element analysis.

In this step, for a standard-scale specimen, and a small-scale specimen having a predetermined size determined optionally by the researcher, a hole expansion test is performed by a punch having a conical angle of 60°, and the above test process is simulated to compare the deformation behavior. In this case, a stress triaxiality value is used as a representative index exhibiting the pattern of deformation behavior.

In examples of the invention, a specimen having a circular shape with a total diameter of 10 mm, and an initial hole diameter of 2 mm was selected as a small-scale specimen. On the other hand, in order to stably fix the specimen in the hole expansion test, the radius of an initial hole was determined so as to be within ¼ of the distance from the center of the initial hole to the edge of the specimen.

In addition, a diameter of the punch, which has a conical angle of 60° and performs the hole expansion, is determined so as not to interfere with fixation of the specimen when evaluated in the range of 1.5 times to 10 times the initial hole diameter depending on the expected hole expansion ratio of an evaluation material.

After a small-scale specimen and a diameter of the punch diameter to be applied to the small-scale specimen were determined through the process as described above, the hole expansion test for the standard-scale specimen and the small-scale specimen was simulated through finite element analysis.

FIG. 1 is a schematic view illustrating the size of a specimen and a hole expansion test apparatus used in the computer simulation of a standard-scale specimen. FIG. 2 is a schematic view illustrating the size of a specimen and a hole expansion test apparatus used in the computer simulation of a small-scale specimen.

As may be seen from FIG. 2, when the hole expansion test for the small-scale specimen is performed actually, a small camera was installed in a direction where the punch is operated to obtain image data for a deformation process, and the image data was processed to be analyzed by the computer.

FIG. 3 is an illustrative view (PEEQ: equivalent plastic strain, TRIAX: stress triaxiality) analyzing the deformation behavior of a standard-scale specimen (a), and a small-scale specimen (b) according to the invention when the hole expansion test is performed through the computer simulation using finite element analysis. FIG. 4 illustrates the deformation behavior of a hole-edge region depending on the hole expansion ratio for a standard-scale specimen, and a small-scale specimen according to the invention when the hole expansion test is performed through the computer simulation using finite element analysis.

In FIG. 4, the term "Inner" means the area under the specimen where the specimen directly contacts the punch in the hole-edge region of the specimen, "Middle" means the central area of the specimen in the hole-edge region of the specimen, and "Outer" means the area opposite to the area where the specimen directly contacts the punch in the hole-edge region of the specimen. Each area in the specimen was schematically shown within the right graph of FIG. 4.

In the hole expansion test, the deformation behavior of uniaxial tensile is a dominant deformation behavior when the stress triaxiality is analyzed in the outer area where fracture initiates. The deformation behavior of uniaxial tensile has a dominant stress triaxiality in the range of 0.3 to 0.5, and in the region having a hole expansion ratio of 20% or more, where most metallic materials rupture, the stress triaxiality is within the range of 0.3 to 0.5 in all of the inner, middle, and outer areas.

Accordingly, when the stress triaxiality of the outer area is within 0.3 to 0.5 in the case of analyzing the deformation behavior of the small-scale specimen in the hole expansion test, and when in the region having a hole expansion ratio of 20% or more, where most metallic materials rupture, the stress triaxiality is within 0.3 to 0.5 in all of the inner, middle, and outer areas, the deformation behavior of the small-scale specimen may be considered to be similar to the deformation behavior in the hole expansion test of the standard-scale specimen.

As may be seen from FIGS. 3(b) and 4(b), it was seen that in the range of 0.3 mm to 0.7 mm in thickness, the deformation behavior of the small-scale specimen is similar to the deformation behavior at the time of deformation in the hole expansion test for the standard-scale specimen.

In light of the above results, the thickness of the small-scale specimen was determined to be 0.5 mm in consideration of the convenience of specimen preparation and the measurable load range of the evaluation apparatus. In this case, an average grain size of the four high-strength steels used in the sample test was within 10 μm, so that grain size effects did not occur within the thickness range of 0.3 mm to 0.7 mm. Therefore, a specific thickness was not excluded in consideration of grain size effects.

When it is considered that a small-scale specimen having the size to be evaluated does not exhibit a similar deformation behavior to the standard-scale specimen as shown in FIG. 4, the stress triaxiality of the small-scale specimen is analyzed repeatedly until reaching the deformation behavior similar to the standard-scale specimen while adjusting an initial hole size in the central area of the corresponding specimen morphology, or a specimen thickness.

In this case, in order to prevent grain size effects causing the difference in mechanical properties when the number of grains is too small in the thickness direction, it is preferable to exclude the thickness of 10 times or less of the grain size of the evaluation material from the evaluation range even when the pattern of deformation behavior is similar by analyzing the stress triaxiality.

Hole Expansion Test and Reliability Evaluation

For a standard-scale specimen, and a small-scale specimen of which the size is determined by the above-described computer simulation, actual evaluation is each performed by the hole expansion test apparatus of FIGS. 1 and 2.

In the present example, there were used four kinds of high-strength steel sheets such as a twinning-induced plasticity (TWIP) steel, a dual-phase (DP) steel, and a transformation-induced plasticity (TRIP) steel, which are mainly applied to automobile steel sheets.

Specifically, the standard hole expansion test was performed by using an Erichsen hydraulic universal forming tester (Model 145-60, Erichsen Co., Germany) having a 50 mm diameter punch with a 60° conical angle. An initial hole having a diameter of 10 mm was manufactured by a punching process at the center of a 90×90 mm square specimen according to ISO 16630 standard. The specimen was fixed to the test equipment with a clamping force of 200 kN, and then the test was performed by expanding the hole at a punch speed of 10 mm/min. Further, the hole expansion test of the small-scale specimen was performed by using a universal testing machine (Model RB-302, R&B Company, Korea) with a 50 mm diameter punch having a 60° conical angle. According to the procedure of the present invention, an initial hole having a diameter of 2 mm was manufactured by a punching process in the center of a circular specimen having a diameter of 10 mm, and the specimen was fixed to the testing equipment with a sufficient clamping force, and then the test was performed by expanding the hole at a punch speed of 1 mm/min.

In addition, by using with a sample having the same material as the specimen before the hole expansion test, the initial holes of the standard-scale specimen and the small-scale specimen for the hole expansion test were processed by a punching process, and the distribution patterns of shearing defects in the hole-edge region generated by the above punching process were each observed through a scanning electron microscope and the similarity of defect distributions was compared with each other.

As a result, as shown in FIGS. 5 and 6, the distribution patterns of shearing defects between the standard-scale specimen and the small-scale specimen were similar to each other. Table 1 below shows the results.

TABLE 1

| Specimen name | Rollover zone, length (ratio) | Shearing zone, length (ratio) | Fracture zone, length (ratio) |
|---|---|---|---|
| Standard-scale specimen | 100 μm (7.3%) | 405 μm (29.5%) | 869 μm (63.2%) |
| Small-scale specimen | 49.2 μm (10.7%) | 153.8 μm (33.5%) | 256.4 μm (55.8%) |

As shown in FIGS. 5 and 6 and Table 1, the standard-scale specimen and the small-scale specimen have the surface of shearing defects having a similar morphology and distribution.

Table 2 below shows the results of measuring the hole expansion ratio of the standard-scale specimen and the small-scale specimen

TABLE 2

| Specimen | Small-scale specimen Hole expansion ratio (%) | Standard-scale specimen Hole expansion ratio (%) |
|---|---|---|
| CR TWIP1100 | 31.63 ± 1.20 | 31.97 ± 3.37 |
| DP980 | 30.96 ± 0.80 | 30.04 ± 2.43 |
| DP780 | 28.92 ± 0.57 | 27.85 ± 0.53 |
| TRIP780 | 22.65 ± 1.38 | 23.95 ± 1.49 |

When an evaluation value for the hole expansion ratio of a small-scale specimen is within the error range of 0.9 times to 1.1 times an evaluation value for the hole expansion ratio of a standard-scale specimen, it may be reliable.

As may be seen from the Table 2, when all of the tested four steels were compared with the standard-scale specimen, CR TWIP1100 steel was in the error range of ±3.00%, DP780 steel was in the error range of ±2.79%, and TRIP780 steel was in the error range of ±2.40%, and it was verified that the stretch-flangeability could be accurately measured within the error range of the evaluation value for the standard-scale specimen.

When stretch-flangeability is evaluated by a specimen having the size of the small-scale specimen determined by the above-described process, specimen size effects may be eliminated. Also, the stretch-flangeability of steel in the research and development stage in which the steel sheet is not mass-produced and the local stretch-flangeability of the sheet material may be effectively measured. Therefore, the evaluation for stretch-flangeability may be performed more effectively when advanced high-strength steel sheets are developed.

According to a method of evaluating stretch-flangeability of sheet metal materials by using the small-scale specimen formed as described above, there are effects that the stretch-flangeability of sheet metal materials may be reliably measured even by using a small amount of material, and the stretch-flangeability in a localized area may be also measured.

Due to this, there are advantages that the stretch-flangeability of the steel being developed may be evaluated rapidly and accurately, thus performing evaluation and feedback, and even when the evaluation for stretch-flangeability is required among existing sheet metal materials, the stretch-flangeability may also be evaluated economically with a small amount of specimen.

In addition, there are advantages that through a procedure of determining the size and morphology of the small-scale specimen without specimen size effects, the morphology of a specimen for evaluation of the stretch-flangeability required by an evaluation party may be determined, and the degree of freedom for a specimen morphology may be increased.

What is claimed is:

1. A method of evaluating stretch-flangeability with a small-scale specimen without specimen size effects, comprising:
   (a) performing a computer simulation of a small-scale specimen having a predetermined size by using finite element analysis to determine a size of the small-scale specimen;
   (b) using a standard-scale specimen having the same material as the small-scale specimen determined in the step (a) to perform a punching process specified in a standard testing method;
   (c) observing a distribution pattern of shearing defects in a hole-edge region of the specimen having performed the punching process, and evaluating a hole expansion ratio;
   (d) comparing the hole expansion ratio and the distribution pattern of shearing defects between the small-scale specimen and the standard-scale specimen to verify measurement reliability for the stretch-flangeability of the small-scale specimen; and
   (e) using a size of the small-scale specimen having verified the measurement reliability to evaluate stretch-flangeability.

2. The method according to claim 1,
   wherein the step (a) comprises analyzing a stress triaxiality of deformation behavior in the hole expansion test of the standard-scale specimen through the computer simulation using finite element analysis to be used as a standard deformation behavior; and
   analyzing the stress triaxiality of deformation behavior in the hole expansion test of the small-scale specimen to verify a morphology and a size validity of the small-scale specimen through comparison with the standard-scale specimen.

3. The method according to claim 1,
   wherein in the step (a), the radius of an initial hole of the small-scale specimen is within ¼ of the distance from a center of the initial hole to an edge of the specimen,
   wherein the punch having a conical angle of 60° used in hole expansion has a diameter in the range of 1.5 times to 10 times the initial hole diameter.

4. The method according to claim 2,
   wherein the deformation behavior of the small-scale specimen simulated by the computer simulation is compared with and the deformation behavior of the standard-scale specimen, and when not similar, the size is adjusted and repeated until being similar, whereby the size of the small-scale specimen is determined.

5. The method according to claim 1,
wherein in the step (a), the minimum value of the thickness of the small-scale specimen is 10 times or more the grain size of the material to be evaluated.

6. The method according to claim 1,
Wherein the standard test method is a method of measuring a standard stretch-flangeability of a sheet metal material, which is the ISO16630 hole expansion ratio test method.

7. The method according to claim 1,
wherein in verifying the measurement reliability of the step (d), the small-scale specimen is evaluated to have reliability when the evaluation value for the hole expansion ratio of the small-scale specimen is 0.9 times to 1.1 times the evaluation value of the standard-scale specimen.

8. The method according to claim 2,
wherein when the deformation behavior of the small-scale specimen is analyzed by the hole expansion test in the computer simulation, the small-scale specimen is evaluated to have a similar deformation behavior to the case of the hole expansion test of the standard-scale specimen when the stress triaxiality in inner, middle and outer areas is within 0.3 to 0.5 in the range of a hole expansion ratio of 20% or more.

9. The method according to claim 4,
wherein the size of the specimen is adjusted by an initial hole size in the center of a specimen morphology and or a specimen thickness.

\* \* \* \* \*